United States Patent [19]

Zoche

[11] Patent Number: 5,087,718

[45] Date of Patent: Feb. 11, 1992

[54] PROCESS FOR THE MANUFACTURE OF KETOXIMOSILANES

[75] Inventor: Günter Zoche, Bonn, Fed. Rep. of Germany

[73] Assignee: Huels Aktiengesellschaft, Marl, Fed. Rep. of Germany

[21] Appl. No.: 460,689

[22] Filed: Jan. 4, 1990

[30] Foreign Application Priority Data

Feb. 10, 1989 [DE] Fed. Rep. of Germany ....... 3903985

[51] Int. Cl.$^5$ .............................................. C07F 7/10
[52] U.S. Cl. ..................................................... 556/422
[58] Field of Search ......................................... 556/422

[56] References Cited

U.S. PATENT DOCUMENTS

| | | | |
|---|---|---|---|
| 3,189,576 | 6/1965 | Sweet | 556/422 X |
| 3,448,136 | 6/1969 | Pande et al. | 556/422 X |
| 3,697,568 | 10/1972 | Boissieras et al. | 556/422 |
| 4,033,991 | 7/1977 | Shinohara et al. | 556/422 X |

Primary Examiner—Paul F. Shaver
Attorney, Agent, or Firm—Felfe & Lynch

[57] ABSTRACT

Ketoximosilanes are prepared by reacting alkyl- or alkenyl-acetoxysilanes with ketoximes in the presence of ammonia. The ketoximosilane reaction products are useful as cross-linking agents for organopolysiloxane compositions.

4 Claims, No Drawings

PROCESS FOR THE MANUFACTURE OF KETOXIMOSILANES

FIELD OF THE INVENTION

This invention relates to a novel process for the preparation of ketoximosilanes. These silicon compounds are particularly useful as cross-linking silicon compounds for the manufacture of compositions which are storable under exclusion of water and, upon exposure to moisture at room temperature, harden into elastomers. Such compositions are obtained by admixing diorganopolysiloxanes having condensable terminal groups and cross-linking silicon compounds.

BACKGROUND OF THE INVENTION AND THE PRIOR ART

It is known to prepare ketoximosilanes by reacting alkyltrichlorosilanes with ketoximes; see, for example, German Auslegeschrift 1 301 140, published European Application 0 082 324, Soviet Patent No. 435 243 and Soviet Patent No. 724 514. The performance of these processes always involves the risk that the ketoxime and ketoximosilane come in contact with inorganic substances of a strong acid nature. The resulting intermediate hydrogen chloride then forms the hydrochloride of the ketoxime. For example, methylethylketoxime boils under normal pressure at 152° C. without decomposing, whereas the hydrochloride thereof vigorously decomposes at 50° to 70° C. Such decompositions, moreover, can be triggered by catalytic amounts of $FeCl_3$, for example. Under such conditions, ketoximosilanes also tend to undergo explosive decompositions. L. J. Tyler reports on two violent explosions of this type in *Chemical Engineering News*, 52 (1974), No. 35, 3.

It is also known to prepare ketoximosilanes by reacting organochlorosilanes with ketoximes in the presence of suitable acid acceptors and solvents; see, for example, U.S. Pat. No. 3,962,160, U.S. Pat. No. 3,441,583, U.S. Pat. No. 3,341,486, U.S. Pat. No. 3,817,909, German Auslegeschrift No. 1 301 140, German Auslegeschrift No. 1 120 640, German Auslegeschrift No. 1255 924, French Patent No. 1,118,495, European Patent No. 0 036 262, published European Application No. 0 293 306, and W. Noll, *Chemie und Technologie der Silikone*, page 342, published by Verlag Chemie, Weinheim 1968).

In these known processes, solid ammonium salts such as ammonium chloride or amine hydrochlorides are obtained as byproducts, depending upon the type of acid acceptor which is used. They precipitate in very finely dispersed form and are therefore relatively difficult to filter or wash out. In these processes, too, there is the danger of the above described explosion-like decompositions, for instance, due to formation of so called "acid nests" or even minor metering errors.

The filtrate obtained by filtering the products formed in the above mentioned processes contains the desired oximosilane, which frequently remains in the sump as a colored substance containing ammonium chloride after the solvent is distilled off. A subsequent distillation of the particular ketoximosilane must take place in a vacuum. This operational step involves a great amount of labor and cost, and is not entirely safe because it approaches the thermal stability of the ketoximosilanes.

OBJECTS OF THE INVENTION

It is an object of the present invention to provide a method of preparing ketoximosilanes which
 (a) does not involve the risk of decompositions or explosions,
 (b) permits a continuous reaction without problems,
 (c) results in a solid substance which is easy to separate, and
 (d) does not require a distillation of the ketoximosilane.

Other objects and advantages of the invention will become apparent as the description thereof proceeds.

DESCRIPTION OF THE INVENTION

I have discovered that the above object is achieved by a process for the preparation of ketoximosilanes of the formula $$(R_1)_n Si[O-N=C(R_2)_2]_{(4-n)} \qquad (I)$$

wherein $R_1$ is alkyl of 1 to 18 carbon atoms or alkenyl of 2 to 18 carbon atoms, n is an integer from 0 to 3, inclusive, and $R_2$ are identical or different alkyls of 1 to 6 carbon atoms, which comprises reacting an acetoxysilane of the formula II $$(R_1)_n Si[OCOCH_3]_{(4-n)} \qquad (II)$$

wherein $R_1$ and n have the meanings previously defined, with a ketoxime of the formula III $$HO-N=C(R_2)_2 \qquad (III)$$

wherein $R_2$ has the meanings previously defined, where the mixture of acetoxysilane and ketoxime is reacted with ammonia in the presence of a solvent for complete conversion into the ketoximosilane, the ammonium acetate released by the reaction is filtered off, and the ketoximosilane is isolated by distilling off the solvent.

In contrast to known processes, such as those disclosed in published European Application No. 0 273 189 and German Patent 37 03 484, the ketoximosilanes are obtained in accordance with the process of the present invention in colorless form and without having to be distilled.

The amount of heat released by the reaction can be easily controlled. For example, if methyl-triacetoxysilane and ethylmethylketoxime are combined at 20° C. in a molar ratio of 1:3 without external cooling, the temperature of the reaction mixture rises only to 38° C. If, in accordance with the present invention, a solvent is used as the reaction medium, the increase in temperature is correspondingly less. The temperature of such solutions, starting at 20° C. rises only to 35° to 45° C. without external cooling, depending upon the rate of addition of the ammonia.

For a discontinuous reaction, the stoichiometric amount of ammonia can be introduced into the solution as a gas.

For a continuous operation, the following very simple method can be used:

The liquid solution of acetoxysilane, ketoxime and solvent is introduced in finely dispersed form into the upper portion of a reactor filled with gaseous ammonia. This can, for example, be effected with the aid of nozzles. By precooling the solution which is sprayed into the reactor, and by altering the solvent proportion, the temperature in the reactor can easily be controlled. The ammonia consumption can be very simply determined by measuring the pressure in the reactor. This pressure measurement is controlling for the continuous ammonia metering and can be coupled thereto. The reaction product which collects in the bottom of the reactor is continuously withdrawn in the form of a suspension.

The ammonium acetate released by the reaction as a solid substance is very easily filtered off in all instances. The filtrate is freed from solvent and other volatile components under as gentle conditions as possible (vacuum) by distillation. Whereas the ketoximosilane remains behind, the distillate can be used again without further treatment.

Examples of suitable solvents are pentane, hexane, heptane, cyclohexane, and 1,1,2-trichloro-1,2,2-trifluoro-ethane.

EXAMPLE 1

Methyl-tris-(ethyl-methyl-ketoximo)-silane

While stirring, 840 ml n-heptane, 132 g (0.6 mol) methyltriacetoxy-silane and 165 g (1.9 mols) of ethyl-methyl-ketoxime are combined in a 2-liter round bottom flask. After cooling the mixture to about 20° C., 2 mols of gaseous ammonia were introduced into the mixture over a period of 1 hour. The precipitated ammonium acetate was vacuum-filtered through a glass frit (G2) and was then washed twice with 240 ml each of n-heptane. The n-heptane was distilled out of the filtrate at about 130 mbar. The last, highly volatile components were removed by rapidly and briefly heating the filtrate to 90° C. at 0.5 mbar.

172 g of methyl-tris-(ethyl-methyl-ketoximo)-silane were obtained in the form of a colorless liquid.

EXAMPLE 2

Vinyl-tris-(ethyl-methyl-ketoximo)-silane

While stirring, 950 ml n-pentane, 139 g (0.6 mol) vinyltriacetoxy-silane and 165 g (1.9 mols) ethyl-methyl-ketoxime where combined in a 2-liter round bottom flask. After cooling the mixture to about 20° C., two mols of gaseous ammonia where introduced into the mixture over a period of 1 hour.

After working up the reaction mixture in analogy to Example 1, 169 g of vinyl-tris-(ethyl-methyl-ketoximo)-silane were obtained in the form of a colorless liquid.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

I claim:

1. In the method of preparing ketoximosilanes of the formula $$(R_1)_n Si[O-N=C(R_2)_2]_{(4-n)}$$

wherein $R_1$ is alkyl of 1 to 18 carbon atoms or alkenyl of 2 to 18 carbon atoms, n is an integer from 0 to 3, inclusive, $R_2$ are identical or different alkyls of 1 to 6 carbon atoms, by reacting an acetoxysilane of the formula $$(R_1)_n Si[OCOCH_3]_{(4-n)}$$

wherein $R_1$ and n have the meanings previously defined, with a ketoxime of the formula $$HO-N=C(R_2)_2$$

wherein $R_2$ has the meanings previously defined, the improvement which comprises reacting a mixture of said acetoxysilane and ketoxime with ammonia in the presence of a solvent for complete conversion into the ketoximosilane, filtering off the ammonium acetate released by the reaction, and isolating the ketoximosilane by distilling off the solvent.

2. The method of claim 1, wherein the mixture of acetoxysilane, ketoxime and solvent is introduced in finely dispersed condition into an ammonia atmosphere.

3. The method of claim 1, wherein said solvent is a volatile, inert organic solvent.

4. The method of claim 2, wherein said solvent is a volatile, inert organic solvent.